US009481895B2

(12) United States Patent
Cearley et al.

(10) Patent No.: US 9,481,895 B2
(45) Date of Patent: Nov. 1, 2016

(54) INTRODUCTION OF MODULAR VECTOR ELEMENTS DURING PRODUCTION OF A LENTIVIRUS

(75) Inventors: Jamie Cearley, Harvest, AL (US); Rusla DuBreuil, Huntsville, AL (US)

(73) Assignee: GE Healthcare Dharmacon, Inc., Lafayette, CO (US)

( * ) Notice: Subject to any disclaimer, the term of this patent is extended or adjusted under 35 U.S.C. 154(b) by 0 days.

(21) Appl. No.: 14/236,083

(22) PCT Filed: Sep. 13, 2012

(86) PCT No.: PCT/US2012/054995
§ 371 (c)(1),
(2), (4) Date: Jan. 30, 2014

(87) PCT Pub. No.: WO2013/043442
PCT Pub. Date: Mar. 28, 2013

(65) Prior Publication Data
US 2014/0193914 A1 Jul. 10, 2014

Related U.S. Application Data

(60) Provisional application No. 61/538,473, filed on Sep. 23, 2011.

(51) Int. Cl.
*C12N 15/63* (2006.01)
*C12N 15/86* (2006.01)
*C12N 15/85* (2006.01)

(52) U.S. Cl.
CPC .............. *C12N 15/86* (2013.01); *C12N 15/85* (2013.01); *C12N 2740/15043* (2013.01); *C12N 2800/30* (2013.01); *C12N 2800/40* (2013.01); *C12N 2800/50* (2013.01)

(58) Field of Classification Search
CPC .. C12N 15/86; C12N 15/85; C12N 2800/30; C12N 2800/40; C12N 2800/50; C12N 2740/15043
See application file for complete search history.

(56) References Cited

U.S. PATENT DOCUMENTS

| 6,410,317 B1 | 6/2002 | Farmer |
| 7,090,837 B2 | 8/2006 | Spencer et al. |
| 7,323,619 B2 | 1/2008 | Baltimore et al. |
| 7,612,195 B2 | 11/2009 | Grueneberg et al. |
| 7,884,200 B2 | 2/2011 | Grueneberg et al. |

(Continued)

FOREIGN PATENT DOCUMENTS

WO 02/00875 A2 1/2002

OTHER PUBLICATIONS

PCT International Preliminary Report on Patentability, The International Bureau of WIPO, Mar. 25, 2014, PCT/US2012/054995.
International Searching Authority, International Search Report and Written Opinion, Nov. 19, 2012.
Extended European Search Report, European Patent Office, Apr. 16, 2015, European Application No. 12834178.1.

(Continued)

*Primary Examiner* — Reza Ghafoorian
(74) *Attorney, Agent, or Firm* — Dorf & Nelson LLP; Scott D. Locke, Esq.

(57) ABSTRACT

Methods and kits for lentiviral production are provided. By separating certain components of the vector including but not limited to promoter, reporter and selection marker preference components from the genetic content of interest, one can create libraries that allow for the efficient generation of custom selected lentiviral vectors.

7 Claims, 11 Drawing Sheets

(56) References Cited

U.S. PATENT DOCUMENTS

| | | |
|---|---|---|
| 2005/0003547 A1 | 1/2005 | Spencer et al. |
| 2008/0120732 A1 | 5/2008 | Elliot |
| 2009/0142839 A1 | 6/2009 | Primiano |
| 2010/0041737 A1 | 2/2010 | Naldini et al. |
| 2010/0256222 A1 | 10/2010 | Kelley et al. |

OTHER PUBLICATIONS

Michel, Gilles et al., Site-specific Gene Insertion Mediated by a Cre-loxP-carrying Lentiviral Vector, Molecular Therapy, vol. 181, No. 10, Jul. 13, 2010.

Moffat, Jason, et al. A Lentiviral RNAi Library for Human and Mouse Genes Applied to an Arrayed Viral High-Content Screen, Cell, vol. 124, No. 6, Mar. 1, 2006.

INTRODUCTION OF MODULAR VECTOR ELEMENTS DURING PRODUCTION OF A LENTIVIRUS

FIELD OF INVENTION

The present invention relates to lentiviruses.

BACKGROUND OF THE INVENTION

Biological vectors have proven to be useful in many applications. Among these applications are whole genome screening, gene function studies, and gene therapy. When using these vectors, one preferably tries to transfer genes efficiently to the desired target cells. In order to increase efficiency, researchers have explored ways to use both viral and non-viral vectors.

One of the areas that researchers have explored with great interest is the use of lentiviral vectors. Lentiviral vectors make use of lentiviral sequences and are a subclass of retroviral vectors. However, unlike other retroviruses, lentiviruses are able to integrate into the genome of both dividing and non-dividing cells. After entry into a cell, the viral genome, which is in the form of RNA, is reverse transcribed to generate DNA, which is then inserted into the host genome. Because lentiviral vectors can cause their sequences to be integrated into non-dividing cells, they are particularly promising for many applications.

With the basic means for working with lentiviruses now well-known to persons of ordinary skill in the art, researchers have created whole genome expression libraries that contain small pieces of the genome in large numbers of vectors such as lentiviruses. These whole genome expression libraries are well-known as useful research tools and are becoming increasingly popular for high content screening, as well as for more focused investigations of gene function.

Currently, whole genome libraries are limited to a static choice of all functional components linked to the genetic content including promoter, reporter, selection marker and more during the production of the library. Unfortunately, under currently known techniques it is both logistically and financially impractical to create whole genome content libraries containing a variety of promoters, reporters and drug selection markers. This is a significant limitation because these components can greatly impact the performance and usefulness of the vectors in any given experimental setup. Thus, there is a need for new ways by which to create lentiviral vectors and libraries that have sufficient levels of variability.

SUMMARY OF THE INVENTION

The present invention is directed to kits and methods for the introduction of modular vector elements on a plurality of vectors that may be brought together through recombination within a packaging cell. The present invention is also directed to libraries that may be used to generate recombined lentiviruses and to libraries that are formed from these modular vectors. Through the use of various embodiments of the present invention, there can be an increase in versatility and choice in efficiently producing lentiviruses. By way of a non-limiting example, in many embodiments it is useful for Cre recombinase to be present in the packaging cell line or introduced into the cell in which recombination is to take place.

According to a first embodiment, the present invention provides a kit for the introduction of modular vector elements comprising: (a) a preference vector; and (b) a content vector, wherein the content vector comprises genomic content of interest. The preference vector and the content vector may be designed such that they are capable of recombining and when combined form a desired lentiviral product. The vectors may also be designed such that the resultant lentivirus may contain only one region of genomic content of interest and only one promoter sequence. Thus, in these embodiments of the kit, the promoter and genomic content of interest are located on different vectors.

According to a second embodiment, the present invention provides a kit for the introduction of modular vector elements comprising: (a) a plurality of preference vectors; (b) a plurality of cells from a cell line; and (c) at least one content vector.

According to a third embodiment, the present invention provides a method for generating a viral vector comprising: (a) introducing a preference vector into a cell; (b) introducing a content vector into the cell; and (c) subjecting the cell to conditions under which the preference vector and the content vector are capable of combining into a plasmid capable of producing a viral transcript. Optionally, the cell comprises packaging plasmids prior to or along with the introduction of the preference vector and/or content vector.

In some embodiments, the present invention provides for the creation of a single whole genome content library for one or more types of content (shRNA, miRNA, ORF, etc.) that can be modified within a packaging cell (or other cells that contain the requisite packaging plasmids). The library may contain any number of promoter, reporter, and selection marker preferences. The mechanism for creating the library relies on the separation of the promoter, reporter, selection marker preference components (i.e. preference vector(s)) from the genetic content (i.e. content vector(s)) onto two independent vectors, e.g., plasmids. These two vectors may be engineered such that independent of each other, neither can form functional viral particles.

Additionally, the two vectors together within a packaging cell line may be designed so that they are unable to form viral particles in the absence of an enzyme that facilitates recombination. In one embodiment, the vectors are designed such that recombination is only possible in the presence of Cre recombinase. Thus, in these embodiments, only when both the preference vector and the content vector, together with the Trans-Lenti Packaging Mix (Generation 3 or 4, or comparable mix) are inside a Cre recombinase expressing packaging cell line will functional viral particles be created. In some embodiments an end user may benefit from the ability to purchase a single content vector or library and then create any "flavor" of viral particles he or she desires by simply selecting the preference vector(s) containing the elements of their choice.

DETAILED DESCRIPTION

Figure 1:
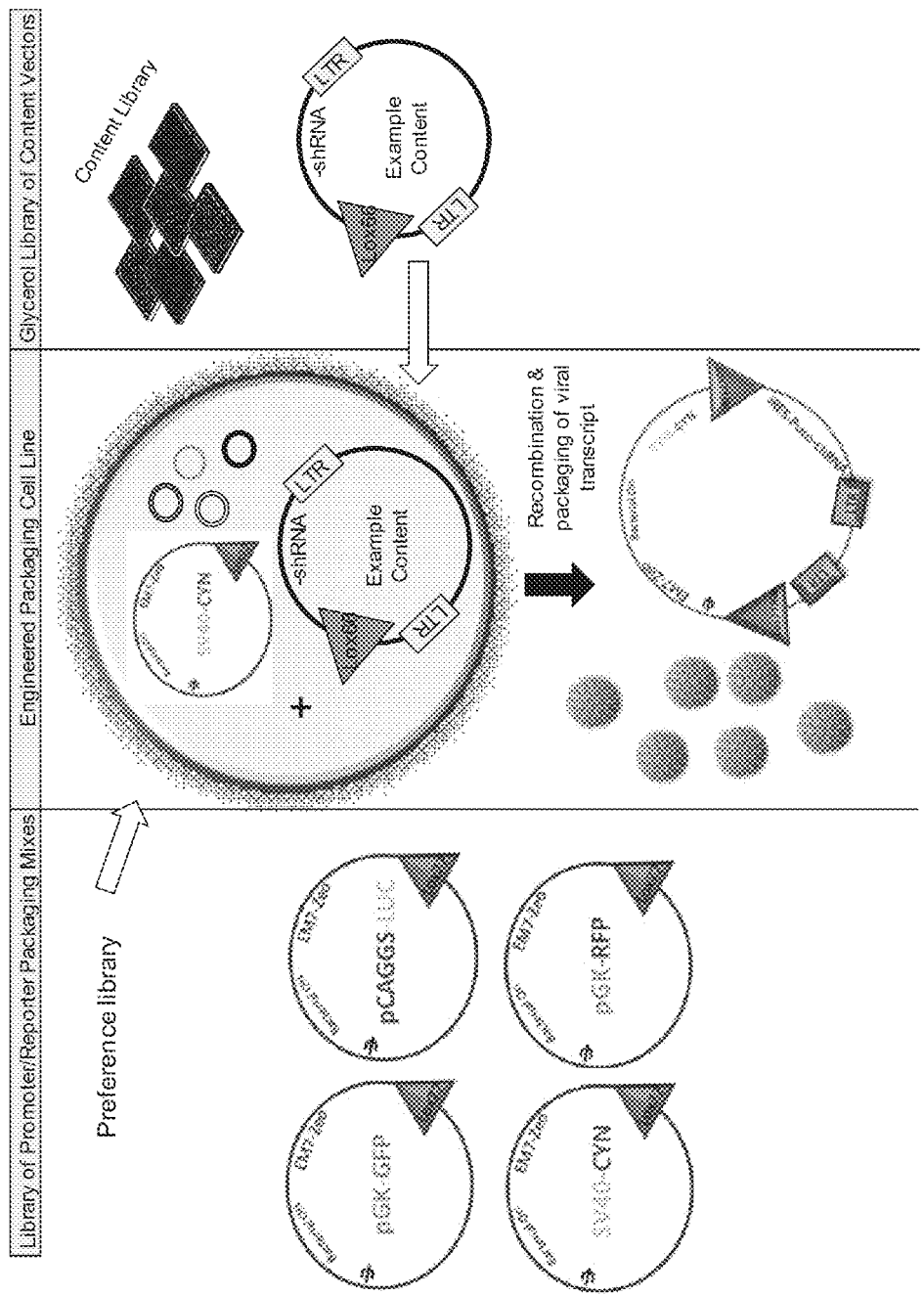
FIG. 1 is a representation of a method according to the present invention.

According to a first embodiment, the present invention provides a kit for the introduction of modular vector elements. The kit comprises a preference vector and a content vector. The preference vector comprises one or more sequences that facilitate or are indicative of expression of a vector. The content vector comprises a sequence that corresponds to genomic content of interest. In some embodiments, the kit comprises a plurality of each of these vectors.

A "vector" may be an agent such as a plasmid, a phage, a virus or a cosmid that may be used to transmit genetic material to a cell or an organism. A "preference vector" is a vector that may contain one, two or all three of a promoter sequence, a selection marker sequence and a reporter sequence. Examples of promoter sequences include but are not limited to the CMV, EF1α, pGK, pCAGGs, SV40, U6 and H1 promoters. Examples of reporter sequences include but are not limited to hrGFP, Blasticidin, Hygromycin, Puromycin, luciferase and eGFP-Puromycin fusion and combinations thereof. In addition to promoter and reporter choices, other elements can also be incorporated including but not limited to IRES, 2a peptide, myc-tag, HA-tag, and FLAG-tag and combinations thereof.

The preference vector may also have a site specific recombination sequence such as Lox77. Furthermore, there may be an EM7-Zeo sequence, which is a synthetic bacterial promoter (EM7) as well as a selection marker (zeo). The EM7-Zeo sequence has an advantage of being small. However, it is a non-limiting example, and other bacterial promoter/selection markers could be used in its place, e.g., Ampicillin, Kanamycin, or Chloramphenicol. Further, there also may be a bacterial Ori sequence, which is a site at which chromosomal replication can begin, and a psi sequence site. Each of these sequences are well-known to persons of ordinary skill in the art and may be accessible through one or more publicly accessible databases such as Entrez and the sequences contained therein are incorporated by reference.

In some embodiments, the preference vector is a plasmid. Examples of plasmids include but are not limited to those that contain pGK-GFP, pCAGGS-LUC, SV40-CYN, and pGK-RFP. These plasmids are fully disclosed in the Entrez. An example of components of the plasmids that may be combined are shown in Table I below:

TABLE I

| Promoter | Reporter | Selection Marker | Other |
| --- | --- | --- | --- |
| pGK | GFP | Puromycin | IRES |
| CMV | RFP | Blasticidin | 2a peptide |
| pCAGGs | Cyn | Hygromycin | Myc-tag |
| EF1alpha | Luciferase | Neomycin | HA-tag |
| U6 | mKate-2 | Hprt | FLAG-tag |

The horizontal rows across provide examples of five sets of combinations of four components. However, as a person of ordinary skill in the art will recognize, the examples of each of the four types of components can be combined in 625 combinations ($5^4$), each of which is within the scope of the present invention, as are the combinations that use other components, e.g., other promoters, reporters, selection markers, etc.

The preference vector may be selected from a preference library that contains one or more preference vectors, e.g., at least 2, at least 3, at least 4, at least 5, at least 10, at least 20, at least 30, at least 50, etc. preference vectors. The entire preference library or a subset of it may be included in a kit. Within a library, preference vectors may differ by only one or one or more of the promoter sequence, selection marker sequence, reporter sequence or other elements. Each preference vector may be stored in a container that is labeled and under conditions that preserve the integrity of the vector.

The content vector comprises genomic content of interest. The phrase "genomic content of interest" refers to a nucleotide sequence that is derived from an organism or is synthetically created (enzymatically and/or chemically) and that is desired to become part of the resultant (also referred to as recombined) lentiviral vector. As with the preference vector, the content vector may, for example, be in the form of a plasmid. The content vector may also contain a site specific recombination sequence, e.g., Lox66, and one or more LTR (long terminal repeat) sequences, e.g. two LTR sequences, one of which is 5' and one of which is 3'. The LTR sequences are flanking sequences that contain cis acting elements that are required for reverse transcription, integration, and expression of the viral genes. The content vector may incorporate sequences from any known organism. These sequences may be incorporated in their native form or may be modified by, for example, one or more insertions, deletions or substitutions.

Additionally, the content vector may be selected from a content library that contains one or more content vectors, e.g., at least 2, at least 3, at least 4, at least 5, at least 10, at least 20, at least 30, at least 50, etc. content vectors. The entire content library or a subset of it may be included in a kit. Within a content library, content vectors may, for example, be designed such that only their genomic content of interest regions are different. Each content vector may be stored in a container that is labeled and under conditions that preserve the integrity of the vector.

The content vector and the preference vector may be generated by any technique that is now known or that comes to be known and that may be appreciated by persons of ordinary skill in the art as being of value for use in connection with the present invention. The techniques include but are not limited to restriction endonuclease digestion, ligation, transformation, PCR, oligo synthesis, and plasmid purification. Examples of techniques that may be used are disclosed in Molecular Cloning: A Laboratory Manual (3 volume set), J. Sambrook, E. F. Fritsch, T. Maniatis, the disclosure of which is incorporated by reference.

In some embodiments, the genomic content of interest of the content vector comprises a sequence that corresponds to an siRNA, an shRNA, cDNA, ORF or an miRNA or a combination thereof. In other embodiments, the content vector may comprise a sequence that is derived from an siRNA, an shRNA, cDNA, ORF or an miRNA. Within a library, each sequence of a particular type may be present, e.g., all miRNAs of a species, or all siRNAs of a particular length (e.g., 19-25 nucleotides) of a species, or all siRNAs of a particular length (e.g., 19-25 nucleotides) that are associated with a particular gene or disorder. The content vector library and/or the preference vector library may be actual libraries of nucleotide sequences or virtual libraries, i.e., computer codes that correspond to the sequences. Additionally, the preference vector library and content vector library may be part of a combined library, wherein each vector is a separate sample or piece of data.

In some embodiments, the kit also comprises viral packaging plasmids. The packaging plasmids may already exist within the cells of a cell line or cell lines of the kit or they may exist separately and need to be introduced into the cell line(s). By way of a non-limiting example, one may use the packaging plasmids from Open Biosystems: TRANS-LENTIVRIAL™ Packaging kit. Packaging plasmids include all of the proteins necessary to package the viral genome into viral particles capable of infection but not replication. As persons of ordinary skill in the art are aware, packaging plasmids can be co-transfected with other vectors. Thus, they may be advantageous for use in combination with the preference vector and the content vector described above, and in some embodiments, preferably, the kit comprises a packaging cell line that already contains these packaging plasmids. Examples of packaging cell lines include but are not limited to HEK293T, 293 (ATCC CCL X), HeLa (ATCC CCL 2), D17 (ATCC CCL 183), MDCK (ATCC CCL 34), BHK (ATCC CCL-10) and CF2TL (ATCC CRL 1430).

According to another embodiment, the present invention provides a method for generating a viral vector. This method, which is illustrated in FIG. 1, comprises introducing a preference vector into a cell; introducing a content vector into the cell; and subjecting the cell to conditions under which the preference vector and the content vector are capable of combining into a viral transcript. As shown in the figure, in this example the packaging plasmids are already within the cell. The cell may have expressed, be expressing and/or be capable of expressing the enzymes and/or other proteins necessary for recombination at the time that the vectors are introduced to the cell.

Also shown in FIG. 1, the preference vector, may be selected from a preference vector library. Non-limiting examples of preference vectors pGK-GFP, SV40-CYN, pGK-RFP and pCAGGS-LUC are shown. The researcher may also select a content vector from the content vector library. Both the content vector and the preference vector are transfected into an engineered packaging cell line. In this case, the packaging plasmids are shown already in the cell line. The genomic content of interest of the content vector may be known prior to introduction into the cell. Alternatively, it may be unknown at the time.

As FIG. 1 also shows, after cotransfection, the preference vector and the content vector combine. Next there is packaging of the viral transcript, which is one recombined sequence that contains the elements of both the preference vector and the content vector. As persons of ordinary skill in the art will recognize, if only one preference vector and one content vector are used at a time, then the recombined vector, also referred to as the viral transcript that is generated can be efficiently produced. If the same preference vector is used with a plurality of different content vectors, then a plurality of lentiviral vectors can be generated to form a lentiviral vector library with a user defined promoter sequence. If a plurality of preference vectors is used with plurality of different content vectors, then a plurality of lentiviral vectors can be generated to form a lentiviral vector library with there being different promoter sequences for different genomic sequences of interest. Depending on the number of different preference vectors used a first subset of the sequences in the resultant library may have a first promoter region associated with it, while a second subset of the sequences in the resultant library may have a second promoter region associated with it. The more different preference vectors that are used, the more different subsets there may be. For example, there may be a plurality, more than two, more than three, more than four, more than five, more than ten, more than twenty, etc.

Figure 2:
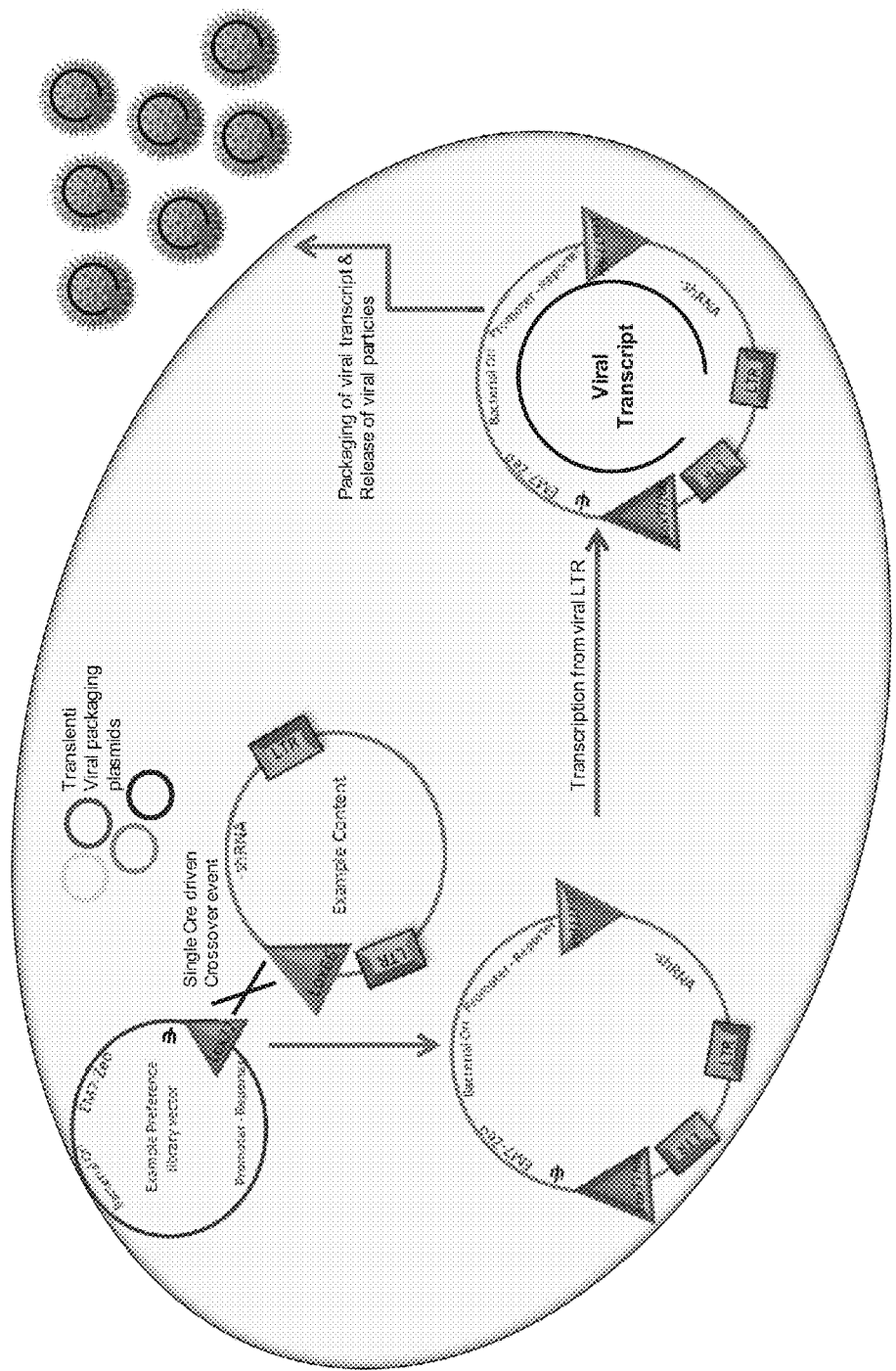
FIG. 2 is a representation of a mechanism of an embodiment of the present invention.

FIG. 2 provides a more detailed representation of the mechanism by which recombination occurs. In the cell are viral packaging plasmids, a preference vector and a content vector. The preference vector comprises a bacterial Ori site, an EM7-Zeo site, a promoter sequence, a reporter sequence and a Lox77 site. The content vector has a LOX66 sequence, two LTR sequences and an shRNA sequence. Conditions are such that there is a single Cre driven crossover event, which results in one circular nucleotide sequence. Following the generation of this sequence, transcription from the LTRs occurs to produce a viral transcript. The viral transcript is then packaged and viral particles are released.

In various embodiments, one may employ strategies to increase viral titer. These strategies may or may not include one or more if not all of: codon optimization of Cre recombinase (which provides a higher level of translation from the messenger RNA, thereby increasing the amount of Cre protein in the cell), inclusion of SV40 origins of replication on the preference and/or content vectors (which allows the plasmid to self-replicate inside of the packaging cell and thereby increase the concentration of that plasmid inside the cell), changing the promoter driving Cre recombinase expression (which allows for a higher level of mRNA expression), and clonally isolating HEK293T-Lenti Cre colonies (which allows for selection of those cells that express Cre at maximum performance level and creation of a uniform population of those cells) for optimal performance. After satisfactory titers are achieved, a content library can be generated using a standard library production protocol. A preference library can be created that would include various promoter, selection marker, and reporter choices through conventional cloning techniques. By way of a non-limiting example the content library could be offered as glycerol stocks, the HEK293T-Lenti Cre cell line as a frozen stock, and the preference vectors included in a packaging mix.

As noted above, in some embodiments, higher quantities of plasmid may be used, which could lead to greater potential for recombination and/or packaging. In one of these embodiments, one may put SV40-Oris on both the preference vector and the content vector in order to increase the overall concentration of these inside of the cell. Alternatively, one may design the preference and the content plasmids such that only where properly recombined the resultant plasmid has a functional SV40-Ori thereby increasing the concentration of the desired recombination only and therefore increasing the packaging level.

As persons of ordinary skill in the art will appreciate, the resultant viral vectors will be effective at entering cells only to the degree that they contain the necessary envelope glycoproteins that facilitate entry into a cell.

The resultant viral vectors may be administered to a cell of interest. If it contains a sequence that corresponds to a functional siRNA, shRNA, miRNA, or cDNA, or an ORF after introduction into the cell, it can modulate and decrease expression of a target gene within a cell. Functionality may be determined empirically or predicted through a bioinformatics technique such as that described in U.S. Patent Publication No. 2005-0255487, published on Nov. 17, 2005, the disclosure of which is incorporated by reference herein. Introduction into the cell can occur in vivo, in vitro or ex vivo. The cells may be prokaryotic or eurkaryotic, e.g., bacteria cells (e.g., *E. coli*), yeast cells or mammalian cells (e.g., human, rodent, chimpanzee, dog, cat, etc.). The cells may for example be obtained from e.g., blood, saliva, semen, hair or skin.

Means for introducing the viral material into a cell may occur by any method that is now known or that comes to be known and that a person of ordinary skill in the art would appreciate as being of use in connection with the present invention. Examples of these methods include but are not limited to transfections, electroporation, microinjection, transduction, cell fusion, DEAE dextran, calcium phosphate precipitation, lipofection, use of a gene gun or a DNA vector transporter.

EXAMPLES

Example 1

Figure 3A:
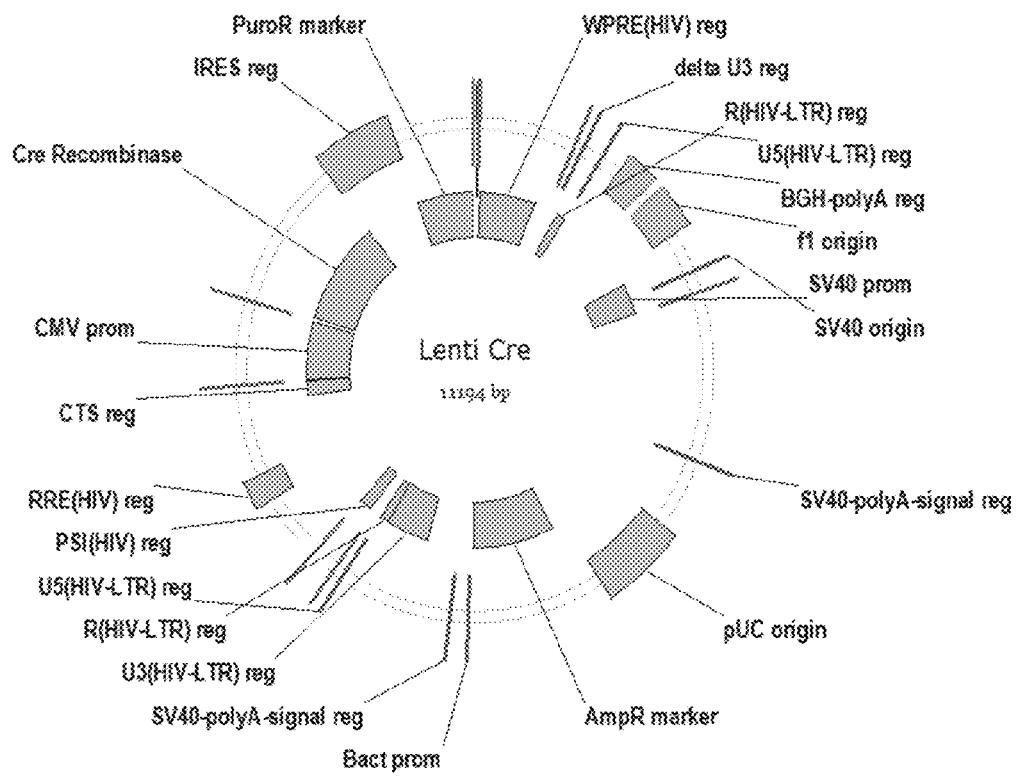
FIGS. 3a and 3b are representations of a lentiviral expression plasmid (Lenti Cre).
Figure 3B:
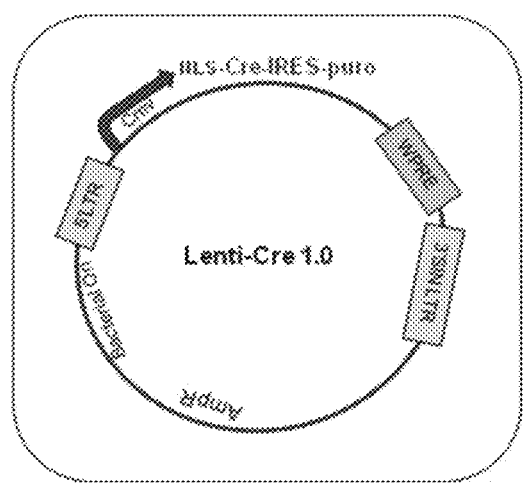

The goal of this experiment was to demonstrate whether an HEK293T viral packaging cell line stably expressing Cre recombinase is capable of recognizing lox sites on a single transfected plasmid and performing a recombination reaction at an appreciable rate. To this end a lentiviral Cre expression plasmid was created (FIGS. 3a and 3b).

Figure 4A:
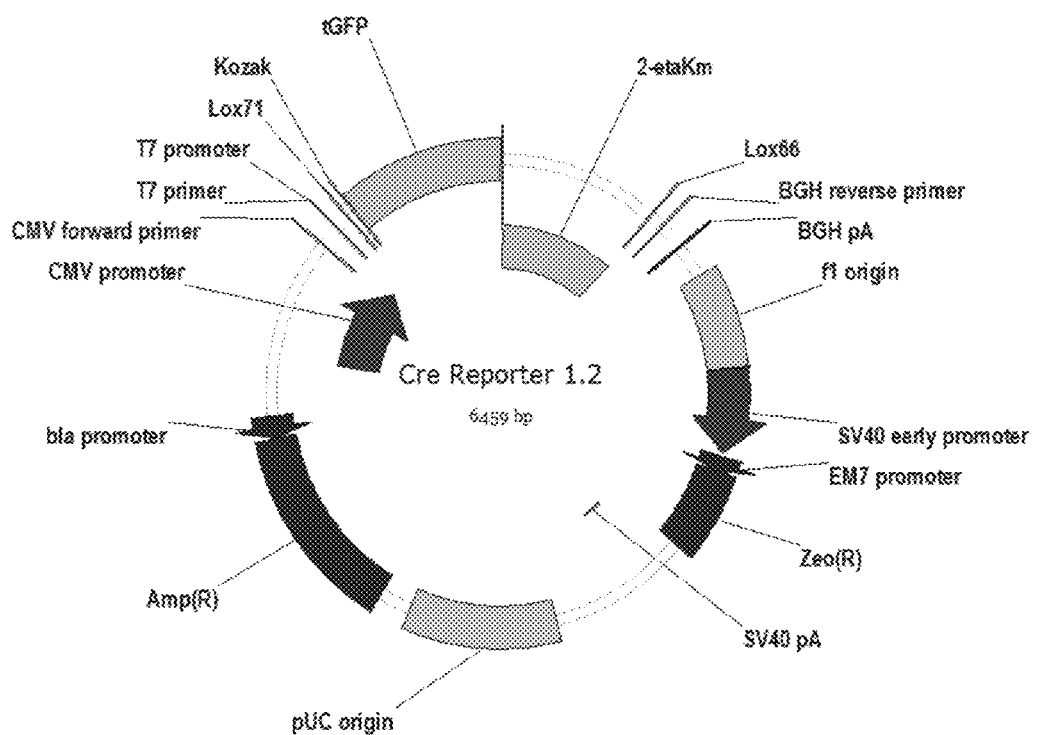
FIGS. 4a and 4b are representations of Cre reporter plasmids (Cre Reporter 1.2).
Figure 4B:
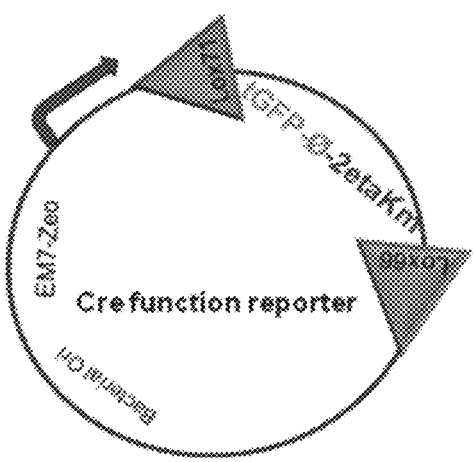

Lenti Cre plasmid was used as the transfer vector in a Trans-lenti packaging reaction. Virus was collected and transduced into HEK293T packaging cells at a rate of 5 ul, 50 ul or 500 ul of viral supernatant. Puromycin selection was begun at 48 hr post transduction and resistant cells resulted (HEK293T-Lenti Cre). To test the ability of Cre recombinase to recognize and recombine lox sites effectively on a transfected plasmid a Cre Reporter vector was constructed (FIGS. 4a and 4b).

The Cre Reporter 1.2 plasmid is designed such that a CMV promoter drives the expression of a lox flanked cassette consisting of tGFP and mKate2 fluorophores in opposing orientations. The lox sites are oriented head to tail so that Cre recombinase action should result in an inversion of the fluorophore cassette. This inversion should result in a switch from tGFP (green) fluorescence expression to mKate2 (red) fluorescence expression.

To test the integrity of the reporter, an in vitro Cre recombinase reaction was performed. Cre Reporter 1.2 plasmid DNA was subjected to Cre Recombinase enzyme (NEB), transformed into Stb12 *E. coli*, and selected on ampicillin containing agar plates. Colonies were picked and assessed for the recombination event via restriction digest.

Figure 5:
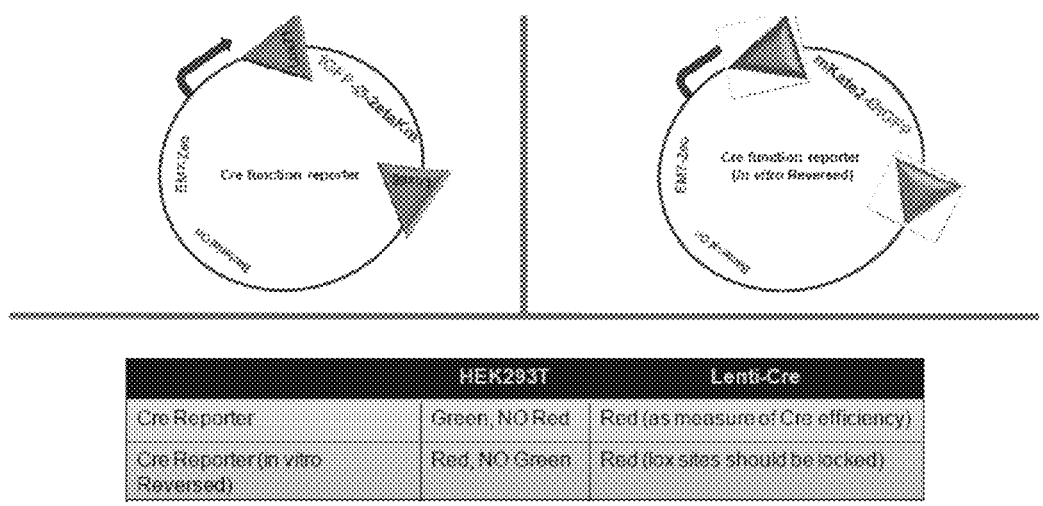
FIG. 5 is a representation of the experimental design of experiment 1.

Finally, the ability of the Cre recombinase expressed in HEK293T-Lenti Cre cells to recombine the Cre Reporter 1.2 fluorophore cassette was tested. Cre Reporter 1.2 or Cre Reporter 1.2 (in vitro reversed) plasmids were transfected into HEK293T or HEK293T-Lenti Cre cells and fluorescence was observed under a microscope. The experimental design is shown in FIG. 5. When using the stock reporter, (upper left of figure) one expects green if Cre is not functioning, and red if Cre performs the recombination reaction. When one uses the construct depicted in the upper left of the figure, the reporter is reversed in vitro in order to create a reporter positive control. This control is clonal and one expects to see red and not green and the lox sites should be locked.

Figure 6:
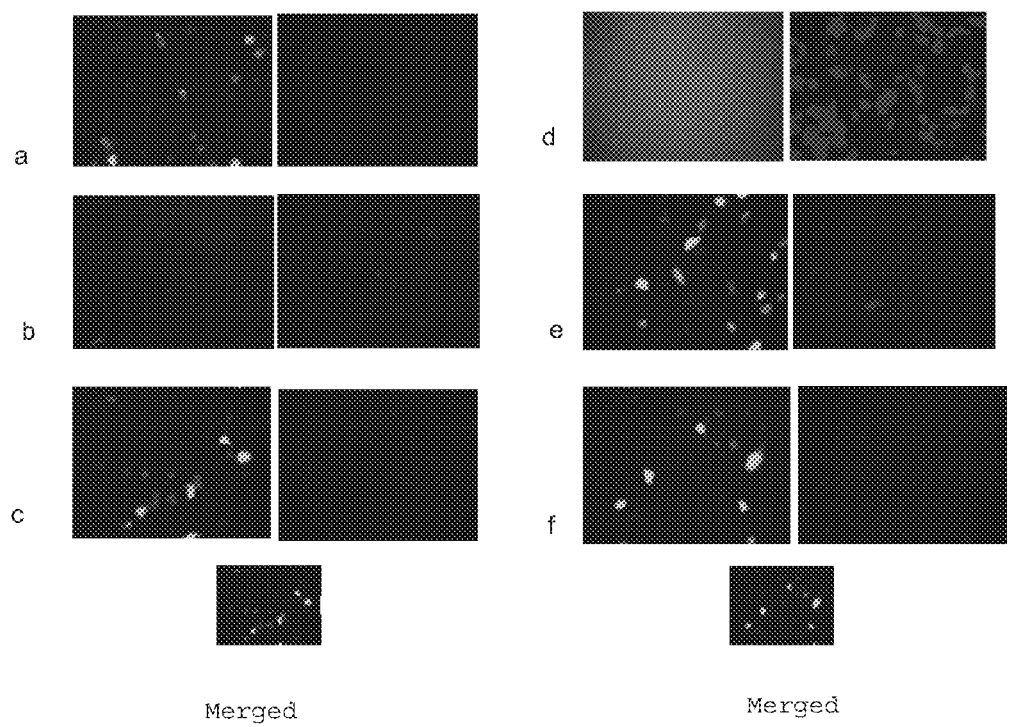
FIG. 6 is a representation of the results of experiment 1, which is an HEK293T-Lenti Cre functionality test. The results shown correspond to (a) HEK 293T+Cre Reporter 1.2; (b) 15× HEK293T-LentiCre (5 ul)+Cre Reporter 1.2; (c) 40× HEK293T-LentiCre (5 ul)+Cre Reporter 1.2; (d) HEK293T+Cre Reporter 1.2 (in vitro Reversed); (e) HEK293T-LentiCre (5 ul)+Cre Reporter 1.2 (in vitro Reversed); (f) 40× HEK293T-LentiCre (500 ul)+Cre Reporter 1.2; and two representations in which systems with plasmids were merged.

Results are shown in FIG. 6, which is a HEK293T-Lenti Cre functionality test: (a) the tGFP reporter is functional; (b) HEK293T-Lenti Cre cells are able to recombine the fluorescence cassette resulting in a green to red conversion; (c) same as (b) at higher magnification; (d) the mKATE2 reporter is functional; (e) the lox sites are able to be flip-flopped to some degree; and (f) same as (c) except at a higher infection level. Within FIG. 6, the fluorescence shown in the left box of each pair of boxes (a)-(f) corresponds to exclusively green fluorescence, whereas the fluorescence shown in the right box of each pair of boxes (a)-(f) corresponds to red fluorescence. Only background fluorescence is detected in the right box of (a), the left box of (b) and the left box of (d). The fluorescence in the two boxes entitled merged correspond to both red and green fluorescence.

Example 2

Prophetic

Figure 7A:
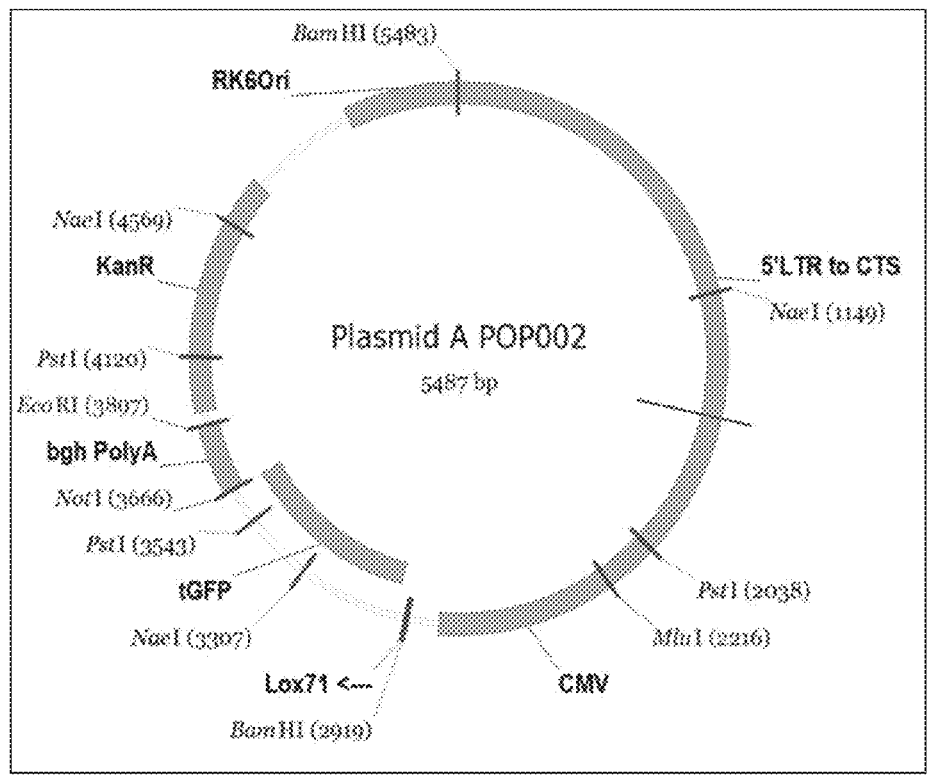
FIGS. 7a, 7b, and 7c are representations of a preference test vector and a content vector, and the resultant lentiviral vector, i.e., a recombined test vector.
Figure 7B:
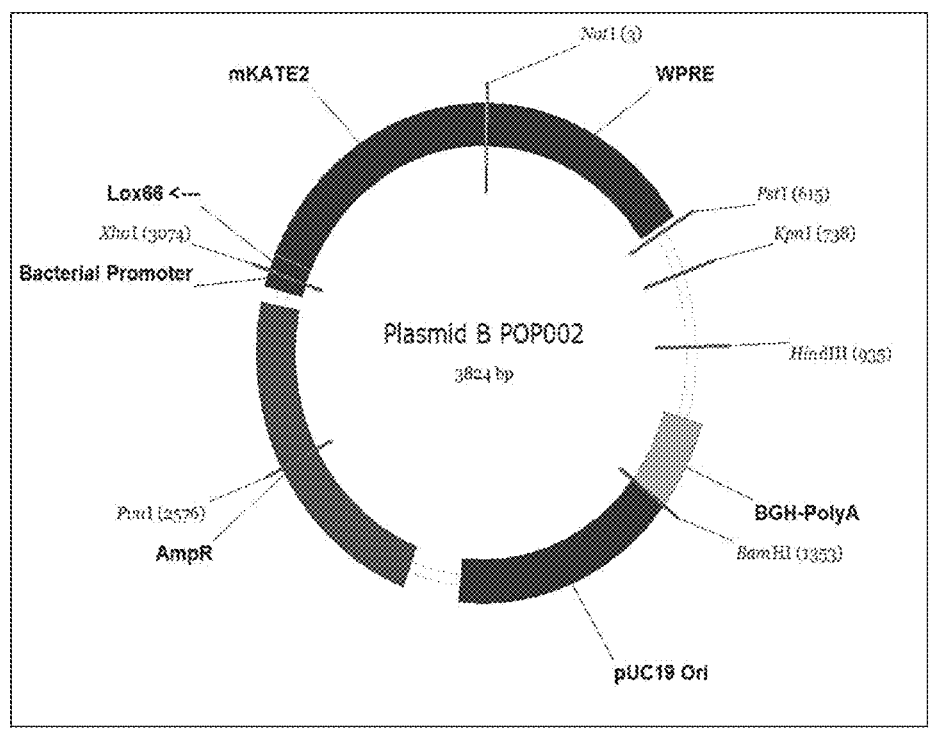
Figure 7C:
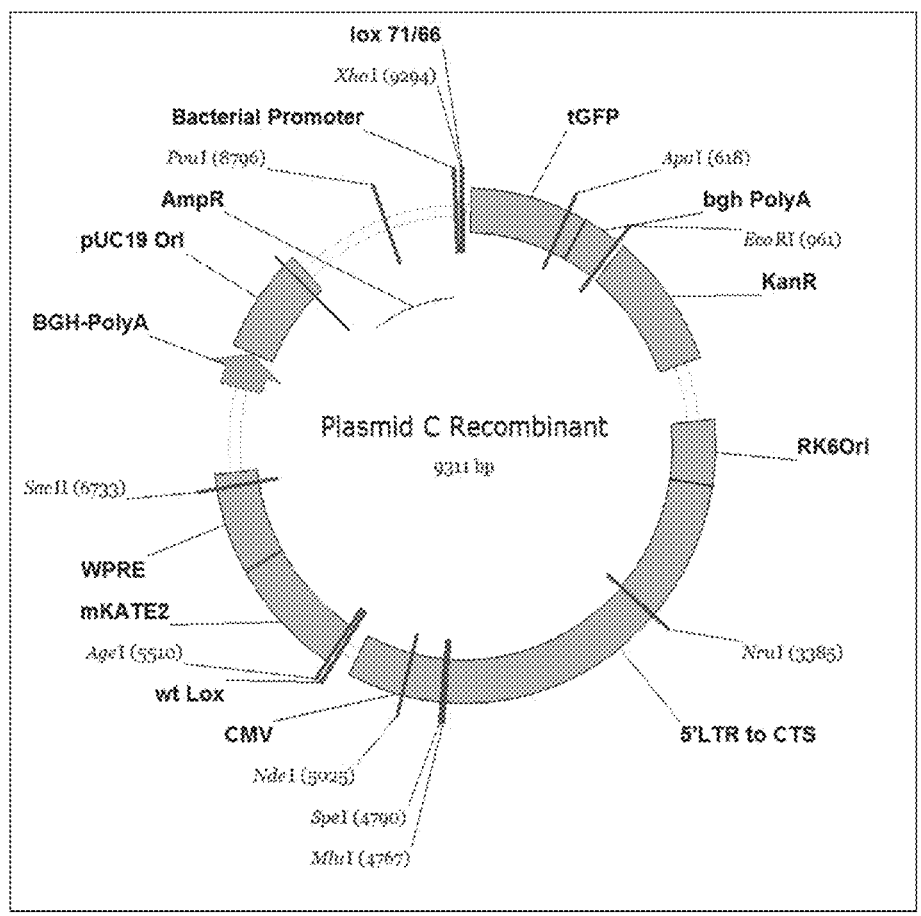

The HEK293T-Lenti Cre cell line stably expressing Cre recombinase can be tested to determine whether it is capable of recognizing lox sites on two independent transfected plasmids and performing a recombination reaction at some appreciable rate. In order to assess this facet of the invention, two vectors may be created: a test preference vector (A) and test content vector (B). See FIGS. 7a, 7b and 7c. The two vectors are designed such that Plasmid A (FIG. 7a) expresses mKate2 when not recombined, and Plasmid B (FIG. 7b) does not express a fluorphore when not recombined. The lox sites are oriented such that a single cross-over event occurs, strands will be exchanged and a single circular plasmid is formed. See Plasmid C (FIG. 7c). After recombination occurs the mKate2 is disassociated from the promoter and instead tGFP may be brought into line for expression. Additional features include the use of an RK6 origin of replication, as well as a Zeocin resistance gene on Plasmid A. This origin of replication is only functional in *E. coli* that contains the Pir116 mutation. Therefore, when conducting an in vitro recombination reaction as was done in Experiment #1 the recombined plasmids can be transformed and selected in *E. coli* that do not have a Pir116 mutation and are selected on Zeocin.

After the vectors are created, the in vitro recombination will be performed. The in vitro product can be tested via restriction digest, PCR, and/or sequencing for cloning accuracy. Finally, Plasmids A+B or Plasmid C (in vitro recombined) will be co-transfected into HEK293T and HEK293T-Lenti Cre cells along with Trans-Lenti packaging mix. The interpretation of the results is shown in Table II below:

TABLE II

| | HEK293T | Enticer |
|---|---|---|
| Plasmid C | Represents 100% Recombination Titer | Represents 100% Recombination Titer + Cre effect |
| Plasmid A + B | Represents 0% Recombination Titer | Represents 0% Recombination Titer + Cre effect |

We claim:
1. A kit for the introduction of modular vector elements comprising:
(a) a preference vector, wherein said preference vector comprises a promoter sequence, a selection marker sequence, and a reporter sequence, wherein the preference vector is selected from the group consisting of pGK-GFP, pCAGGS-LUC, SV40-CYN and pGK-RFP and the preference vector further comprises an Ori site and an EM7-Zeo site; and (b) a content vector, wherein said content vector comprises a genomic content of interest, a first LTR sequence that is 5' of the genomic content of interest and a second LTR sequence that is 3' of the genomic content of interest, and wherein said content vector does not comprise any promoter sequence and said preference vector does not comprise said genomic content of interest and further wherein said preference vector contains one preference vector site specific recombination sequence and said content vector contains one content vector site specific recombination sequence, wherein the preference vector and the content vector are capable of a single cross-over event at the preference vector site specific recombination sequence and the content vector site specific recombination sequence to form a lentiviral vector, wherein the lentiviral vector comprises the preference vector and the content vector.

2. The kit according to claim 1, further comprising a plurality of cells from an engineered packaging cell line.

3. The kit according to claim 1, wherein the genomic content of interest comprises a nucleotide sequence of an siRNA, an shRNA, an miRNA, a cDNA or an ORF.

4. The kit according to claim 1, further comprising viral packaging plasmids.

5. A method for generating a viral vector comprising;
(a) introducing a preference vector, into a cell, wherein the cell comprises one or more packaging plasmids, and the preference vector contains one preference vector site specific recombination sequence;

(b) introducing a content vector into said cell, wherein said content vector comprises a sequence that corresponds to genomic content of interest, one content vector site specific recombination sequence, a first LTR sequence 5' of the genomic content of interest and a second LTR sequence 3' of the genomic content of interest; and (c) subjecting said cell to conditions under which the preference vector and the content vector are capable of combining into a viral transcript through a single cross-over event at the one preference vector site specific recombination sequence and the one content vector site specific recombination sequence, wherein said viral transcript is a lentiviral vector, wherein the lentiviral vector comprises the preference vector and the content vector, and wherein the cell expresses Cre recombinase and each of the content vector site specific recombination sequence and the preference vector site specific recombination sequence is capable of being recognized by Cre recombinase.

6. The kit of claim 1, wherein the content vector site specific recombination sequence is Lox66 and the preference vector site specific recombination sequence is Lox77.

7. The kit of claim 6, wherein the Ori site of the preference vector is SV40-Ori and the content vector contains an SV40-Ori site.

* * * * *